(12) United States Patent
Suh et al.

(10) Patent No.: US 10,888,844 B2
(45) Date of Patent: Jan. 12, 2021

(54) CATALYST FOR OXIDATIVE DEHYDROGENATION, METHOD OF PREPARING CATALYST, AND METHOD OF PERFORMING OXIDATIVE DEHYDROGENATION USING CATALYST

(71) Applicant: LG CHEM, LTD., Seoul (KR)

(72) Inventors: Myung Ji Suh, Daejeon (KR); Dong Hyun Ko, Daejeon (KR); Kyong Yong Cha, Daejeon (KR); Dae Heung Choi, Daejeon (KR); Ye Seul Hwang, Daejeon (KR); Jun Kyu Han, Daejeon (KR); Sun Hwan Hwang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 16/301,403

(22) PCT Filed: Apr. 12, 2018

(86) PCT No.: PCT/KR2018/004269
§ 371 (c)(1),
(2) Date: Nov. 13, 2018

(87) PCT Pub. No.: WO2018/190641
PCT Pub. Date: Oct. 18, 2018

(65) Prior Publication Data
US 2019/0329226 A1   Oct. 31, 2019

(30) Foreign Application Priority Data

Apr. 12, 2017   (KR) .......................... 10-2017-0047503
Apr. 11, 2018   (KR) .......................... 10-2018-0042150

(51) Int. Cl.
*B01J 21/04*   (2006.01)
*B01J 23/80*   (2006.01)
(Continued)

(52) U.S. Cl.
CPC ............... *B01J 23/80* (2013.01); *B01J 21/04* (2013.01); *B01J 35/0026* (2013.01);
(Continued)

(58) Field of Classification Search
None
See application file for complete search history.

(56) References Cited

U.S. PATENT DOCUMENTS 3,671,606 A   6/1972   Manning
3,849,545 A   11/1974   Miklas
(Continued)

FOREIGN PATENT DOCUMENTS

CN   105582954      5/2016
EP   3269448 A2    1/2018
(Continued)

OTHER PUBLICATIONS

Supplementary Search Report of European Patent Office in Appl'n No. EP18784965, dated Jun. 27, 2019.
(Continued)

*Primary Examiner* — Colin W. Slifka
(74) *Attorney, Agent, or Firm* — Dentons US LLP

(57) ABSTRACT

Provided is a catalyst for oxidative dehydrogenation, a method of preparing the catalyst, and a method of performing oxidative dehydrogenation using the catalyst. The catalyst for oxidative dehydrogenation has improved durability and fillability by including a porous support coated with a metal oxide ($AB_2O_4$) according to Equation 1 of the present invention, wherein the metal oxide exhibits activity during oxidative dehydrogenation. Therefore, when the catalyst is used in oxidative dehydrogenation of butene, the conversion rate of butene and the selectivity and yield of butadiene may be greatly improved.

7 Claims, 1 Drawing Sheet

(51) Int. Cl.
*B01J 35/00* (2006.01)
*B01J 35/02* (2006.01)
*B01J 35/08* (2006.01)
*B01J 35/10* (2006.01)
*B01J 37/00* (2006.01)
*B01J 37/02* (2006.01)
*B01J 37/03* (2006.01)
*B01J 37/08* (2006.01)
*C07C 5/48* (2006.01)
*C07C 11/167* (2006.01)

(52) U.S. Cl.
CPC .......... *B01J 35/023* (2013.01); *B01J 35/026* (2013.01); *B01J 35/08* (2013.01); *B01J 35/1076* (2013.01); *B01J 37/0018* (2013.01); *B01J 37/0036* (2013.01); *B01J 37/0221* (2013.01); *B01J 37/0236* (2013.01); *B01J 37/038* (2013.01); *B01J 37/08* (2013.01); *C07C 5/48* (2013.01); *C07C 11/167* (2013.01)

(56) References Cited

U.S. PATENT DOCUMENTS

| | | | |
|---|---|---|---|
| 3,860,650 | A | 1/1975 | Becker et al. |
| 3,998,760 | A | 12/1976 | Christmann et al. |
| 4,077,912 | A | 3/1978 | Dolhyj et al. |
| 4,542,113 | A | 9/1985 | Meyer et al. |
| 4,658,074 | A | 4/1987 | Bajars et al. |
| 6,165,936 | A | 12/2000 | Yamada et al. |
| 8,513,479 | B2 | 8/2013 | Chung et al. |
| 9,550,174 | B2 | 1/2017 | Kwon et al. |
| 2010/0089798 | A1 | 4/2010 | Baudot et al. |
| 2012/0059208 | A1* | 3/2012 | Mamedov ............... B01J 37/03 585/625 |
| 2013/0158325 | A1* | 6/2013 | Kwon .................. C07C 5/3332 585/625 |
| 2018/0333702 | A1* | 11/2018 | Suh ........................ B01J 35/04 |

FOREIGN PATENT DOCUMENTS

| | | |
|---|---|---|
| EP | 3437739 A2 | 2/2019 |
| JP | S49-079988 | 8/1974 |
| JP | S51-125001 | 11/1976 |
| JP | S58-181726 | 10/1983 |
| JP | H11-043380 | 2/1999 |
| JP | 2013536066 | 9/2013 |
| KR | 10-0847206 | 7/2008 |
| KR | 10-1071230 | 10/2011 |
| KR | 10-2012-0009687 | 2/2012 |
| KR | 10-2012-0073998 | 7/2012 |
| KR | 10-1340620 | 12/2013 |
| KR | 10-2014-0082869 | 7/2014 |
| KR | 10-2017-0138124 | 12/2017 |
| WO | WO-2017099411 A1 * 6/2017 ............. B01J 21/02 |
| WO | 2017/171441 | 10/2017 |
| WO | 2017/183829 | 10/2017 |

OTHER PUBLICATIONS

International Search Report and the Written Opinion of PCT/KR2018/004269, dated Jul. 19, 2018.
Office Action of Japanese Patent Office in Appl'n No. 2019-502067 dated Nov. 26, 2019.
XP-002791808; "Catalyst Carriers—Typical Properties," Technical Bulletin, NonPro Catalyst Carriers, Saint Gobain NorPro (Oct. 1, 2018), 5 pages.
Son et al., "Synthesis and Study on Catalytic Activity of Spinel Metallic Oxides in Styrene Preparation from Ethylbenzene," e-Journal of Surface Science and Nanotechnology 10:263-267 (2012).

* cited by examiner

US 10,888,844 B2

CATALYST FOR OXIDATIVE DEHYDROGENATION, METHOD OF PREPARING CATALYST, AND METHOD OF PERFORMING OXIDATIVE DEHYDROGENATION USING CATALYST

CROSS-REFERENCE TO RELATED APPLICATIONS

This application is a National Stage Application of International Application No. PCT/KR2018/004269 filed on Apr. 12, 2018, which claims priority to Korean Patent Application No. 10-2017-0047503 filed on Apr. 12, 2017 and Korean Patent Application No. 10-2018-0042150 re-filed on Apr. 11, 2018, based on the priority of the above patent, in the Korean Intellectual Property Office, the disclosures of each of which are incorporated herein by reference.

TECHNICAL FIELD

The present invention relates to a catalyst for oxidative dehydrogenation, a method of preparing the catalyst, and a method of performing oxidative dehydrogenation using the catalyst. More specifically, the present invention relates to a catalyst for oxidative dehydrogenation having improved durability by including a porous support coated with a metal oxide within a specific content range, wherein the metal oxide exhibits activity during oxidative dehydrogenation, and to a method of preparing the catalyst, and a method of performing oxidative dehydrogenation using the catalyst. According to the present invention, when the catalyst is used in preparation of butadiene, the conversion rate of butene and the selectivity and yield of butadiene may be greatly improved.

Background Art 1,3-butadiene, a major basic fraction, is a representative raw material used in preparation of synthetic rubber, and the price thereof fluctuates rapidly in connection with supply and demand of the petrochemical industry. Examples of the method of preparing 1,3-butadiene include naphtha cracking, direct dehydrogenation of normal butene, oxidative dehydrogenation of normal butene, and the like.

According to the method of preparing 1,3-butadiene by oxidative dehydrogenation of normal butene, butene and oxygen react in the presence of a metal oxide catalyst to generate 1,3-butadiene and water. In this case, water generated as a result of the reaction is stable. Thus, the method is thermodynamically very advantageous. In addition, since oxidative dehydrogenation of normal butene is an exothermic reaction unlike direct dehydrogenation, reaction may be performed at a low temperature. Thus, 1,3-butadiene may be obtained in high yield while reducing energy consumption. In addition, in the case of oxidative dehydrogenation, since an oxidizing agent is added, the generation amount of carbon deposits which shorten the catalyst life by poisoning the catalyst is reduced. Further, since removal of the oxidizing agent is easy, the method of preparing 1,3-butadiene using oxidative dehydrogenation is very suitable for commercialization.

In general, a metal oxide catalyst for oxidative dehydrogenation is extrusion-molded in the form of pellets having increased mechanical strength to improve the fillability and durability of the catalyst in a fixed bed reactor, and then input to the reactor. At this time, an excess of organic or inorganic binder is mixed to improve the weak cohesive strength of the catalyst in powder form. In this case, the yield of butadiene and selectivity for butadiene may be lowered due to side reactions caused by the binder, and active materials may be lost when the catalyst is added. Therefore, a method for solving these problems is required.

PRIOR ART DOCUMENTS

Patent Documents

KR 10-0847206 B1
KR 10-1340620 B1

DISCLOSURE

Technical Problem

Therefore, the present invention has been made in view of the above problems, and it is one object of the present invention to provide a catalyst for oxidative dehydrogenation having improved durability and fillability by including a porous support coated with a metal oxide within a specific content range according to a predetermined method, wherein the metal oxide exhibits activity during oxidative dehydrogenation. Accordingly, when the catalyst is used in preparation of butadiene, conversion rate, selectivity, and yield may be improved.

It is another object of the present invention to provide a method of preparing the catalyst for oxidative dehydrogenation and a method of performing oxidative dehydrogenation using the catalyst according to the present invention.

The above and other objects can be accomplished by the present disclosure described below.

Technical Solution

In accordance with one aspect of the present invention, provided is a catalyst for oxidative dehydrogenation having a porous support coated with $AB_2O_4$ as an active ingredient for oxidative dehydrogenation, wherein the catalyst has a composition satisfying Equation 1 below:

$$X \text{ wt \%} + Y \text{ wt \%} = 100 \text{ wt \%}, \quad \text{[Equation 1]}$$

wherein X represents the content of $AB_2O_4$ and is 5 or more and less than 30, and Y represents the content of the porous support and is more than 70 and 95 or less, wherein A is one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), and B is iron (Fe).

In accordance with another aspect of the present invention, provided is a method of preparing a catalyst for oxidative dehydrogenation, including a step of preparing $AB_2O_4$ powder as an active ingredient for oxidative dehydrogenation; a step of preparing a catalyst slurry by dispersing the $AB_2O_4$ powder in distilled water; a step of coating a porous support with the catalyst slurry; and a step of drying the catalyst slurry-coated porous support to obtain a catalyst for oxidative dehydrogenation, wherein the obtained catalyst has a composition satisfying Equation 1.

In accordance with yet another aspect of the present invention, provided is a method of preparing butadiene, including a step, in which oxidative dehydrogenation is performed by passing reactants including oxygen and a C4 mixture containing normal butene through a reactor filled with the catalyst for oxidative dehydrogenation.

Advantageous Effects

As apparent from the foregoing, the present invention advantageously provides a catalyst for oxidative dehydrogenation, a method of preparing the catalyst, and a method of performing oxidative dehydrogenation using the catalyst. According to the present invention, a reactor can be easily filled with the catalyst, loss of an active ingredient can be minimized during addition of the catalyst, and the durability of the catalyst can be improved. Therefore, when the catalyst is used to prepare butadiene, the conversion rate of butene and the selectivity and yield of butadiene can be greatly improved.

BEST MODE

Figure 1A:
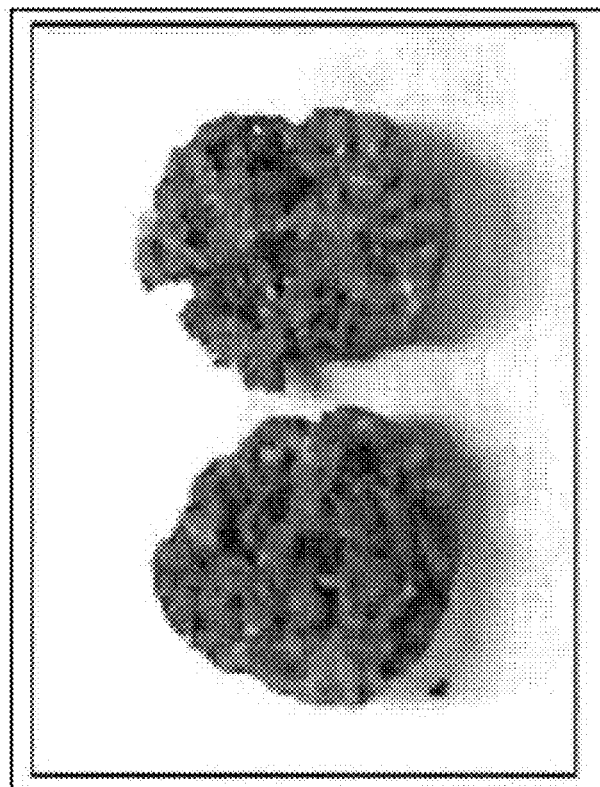
FIGS. 1A and 1B are images showing the surface (FIG. 1A) and cross section (FIG. 1B) of the catalyst for oxidative dehydrogenation prepared according to an embodiment of the present invention.

Hereinafter, the catalyst for oxidative dehydrogenation according to the present invention and the method of preparing the same will be described in detail.

The catalyst for oxidative dehydrogenation according to the present invention has a porous support coated with $AB_2O_4$ as an active ingredient for oxidative dehydrogenation, wherein the catalyst has a composition satisfying Equation 1 below:

$$X \text{ wt \%} + Y \text{ wt \%} = 100 \text{ wt \%}, \quad \text{[Equation 1]}$$

wherein X represents the content of $AB_2O_4$ and is 5 or more and less than 30, and Y represents the content of the porous support and is more than 70 and 95 or less, wherein A represents a divalent cation metal and specific examples thereof include one or more selected from the group consisting of copper (Cu), radium (Ra), barium (Ba), strontium (Sr), calcium (Ca), beryllium (Be), zinc (Zn), magnesium (Mg), manganese (Mn), and cobalt (Co), and B is iron (Fe).

In Equation 1, X may be, for example, 5 or more and less than 30, or 5 to 28, more preferably 7 to 27, 7 to 20, 7 to 18, or 7 to 14. Within this range, reaction efficiency may be excellent, and yield, selectivity, and conversion rate may be improved.

In Equation 1, Y may be, for example, more than 70 and 95 or less, or 72 to 95, more preferably 73 to 93, 80 to 93, 82 to 93, or 86 to 93. Within this range, since the amount of the catalyst to be used is appropriate, reaction efficiency may be excellent, and reaction heat may be easily controlled. Thus, the yield of butadiene and selectivity for butadiene may be improved.

The $AB_2O_4$ is a metal oxide exhibiting activity during oxidative dehydrogenation. For example, the $AB_2O_4$ may be a zinc ferrite ($ZnFe_2O_4$), wherein A is Zn, and B is Fe. The zinc ferrite exhibits excellent activity during oxidative dehydrogenation of normal butene and suppresses generation of side reaction. Thus, when the zinc ferrite is used, selectivity for 1,3-butadiene may be increased.

For example, the $AB_2O_4$ may have an average particle diameter of 250 μm or less, 0.1 to 250 μm, 0.1 to 75 μm, 45 μm or less, 45 to 250 μm, or 100 to 250 μm, preferably 70 μm or less, 50 μm or less, or 45 μm or less. Within this range, the catalyst has excellent activity, and thus reaction efficiency may be improved.

For example, the porous support may have an average particle diameter of 3 mm or more, 3 to 9 mm, or 4 to 6 mm, preferably 3 to 5 mm or 6 to 9 mm. Within this range, reaction efficiency is excellent, and thus conversion rate and selectivity may be improved.

For example, the porous support may have an average pore size of 50 to 200 μm or 100 to 150 μm. Within this range, the catalyst may be easily coated with $AB_2O_4$ powder, and desorption of the powder may be prevented.

In the present invention, average particle diameter and average pore size may be measured using, for example, a scanning electron microscope.

For example, the porous support may have a packing density of 0.4 to 3 g/cm$^3$, or more than 0.4 and less than 3 g/cm$^3$, preferably 0.7 to 2.0 g/cm$^3$, more preferably 0.8 to 1.5 g/cm$^3$. Within this range, reaction efficiency of oxidative dehydrogenation may be excellent, and reaction heat may be easily controlled. Therefore, the yield of butadiene and selectivity for butadiene may be improved.

In the present invention, packing density is calculated by dividing mass capable of filling 100 cc into a tubular measuring cylinder by the volume value of 100 cc.

The porous support is preferably in the form of a sphere, pellet, or hollow bar. In this case, reaction efficiency is excellent, and thus yield, selectivity, and conversion rate may be improved.

For example, the porous support may be one or more selected from the group consisting of alumina, silica, and zirconia, preferably alumina or silica. In this case, the mechanical strength required to fill a reactor may be appropriate, and side reaction may be reduced.

For example, the catalyst may further include an organic or inorganic binder for the purpose of improving the cohesive strength of the $AB_2O_4$ powder, which is an active ingredient for oxidative dehydrogenation. In this case, the binder may be contained in an amount of 30 parts by weight or less, 0.1 to 20 parts by weight, or 0.1 to 10 parts by weight based on 100 parts by weight of the $AB_2O_4$. Within this range, the wear resistance of the catalyst may be improved without significantly lowering the reaction efficiency of oxidative dehydrogenation.

For example, the binder may include aluminum-silicate, methylcellulose, hydroxypropyl methylcellulose, or both. When the binder is contained in an appropriate amount, the wear resistance of the catalyst may be improved without significantly lowering the reaction efficiency of oxidative dehydrogenation.

As another example, the catalyst may be a binder-free catalyst. In this case, side reaction, which may be caused by a binder, does not occur, and thus the conversion rate of normal butene and selectivity for butadiene may be greatly improved. In addition, feed of a certain component may be omitted, thereby shortening the production process of the catalyst and reducing production costs.

In the present invention, binder-free indicates that, when a catalyst is prepared, an organic or inorganic binder is not included and/or a catalyst is prepared without a binder.

For example, the method of preparing a catalyst for oxidative dehydrogenation according to the present invention includes a step of preparing $AB_2O_4$ powder as an active ingredient for oxidative dehydrogenation; a step of preparing a catalyst slurry by dispersing the $AB_2O_4$ powder in distilled water; a step of coating a porous support with the catalyst slurry; and a step of drying the catalyst slurry-coated porous support to obtain a catalyst for oxidative dehydrogenation, wherein the obtained catalyst has a composition satisfying Equation 1. Hereinafter, the method of preparing the catalyst will be described in detail for each step.

In the present invention, the step of preparing $AB_2O_4$ powder as an active ingredient for oxidative dehydrogenation may include, for example, a step of preparing a metal precursor aqueous solution including a metal precursor A and a metal precursor B; a step of adding the metal precursor aqueous solution and a basic aqueous solution, such as aqueous ammonia or an aqueous solution of sodium hydroxide, for maintaining pH at 7 to 10 to the coprecipitation bath to coprecipitate metal A and metal B; and a step of drying and burning the coprecipitation solution after completion of coprecipitation.

For example, the basic aqueous solution may be one or more selected from aqueous ammonia and an aqueous solution of sodium hydroxide, preferably aqueous ammonia.

The metal precursor A and the metal precursor B are not particularly limited as long as the precursors are metal precursors commonly used in the art. Each precursor may be selected from the nitrate, sulfate, chloride, carbonate salt, and acetate of the metal A or B, and hydrate forms thereof may be possible.

For example, the metal precursor A may be a zinc precursor exhibiting high activity during oxidative dehydrogenation, and more specifically, may be one or more selected from zinc nitrate, zinc chloride, and zinc sulfate.

The metal precursor B may be an iron precursor, and more specifically, may be one or more selected from iron nitrate and iron chloride, without being limited thereto.

When the basic aqueous solution and the metal precursors A and B are added dropwise for coprecipitation, it may be preferable to maintain pH at 7 to 10, 7 to 9, or 7.5 to 8.5 so as to minimize formation of crystal structure inactive in oxidative dehydrogenation and stably coprecipitate.

In addition, the amount of each of the metal precursors A and B may be adjusted so that the molar ratio of the metal precursor A to the metal precursor B is, for example, 1:1.5 to 3. Within this range, an $AB_2O_4$ catalyst exhibiting excellent reaction activity during oxidative dehydrogenation may be prepared.

When the metal precursor aqueous solution is added dropwise, the solution is preferably added dropwise at a constant rate while agitating a coprecipitation bath to efficiently coprecipitate the metal A and the metal B.

Further, after all of the metal precursors A and B are added dropwise, a stirring step, an aging step, or a stirring/aging step may be further performed so that sufficient coprecipitation may be performed.

After coprecipitation of the metal A and the metal B is completed, the coprecipitation solution is filtered to separate solid components, and the separated solid components are then dried and burned to obtain $AB_2O_4$ in powder form. In this case, impurities are removed and high purity $AB_2O_4$ powder may be obtained, and the catalytic activity may be improved.

The drying and burning are not particularly limited as long as the drying and burning are within the range usually practiced in the art. For example, the drying may be performed at 60 to 200° C. for 10 to 24 hours, and the burning may be performed at 350 to 800° C. or 400 to 700° C. for 1 to 40 hours or 3 to 18 hours.

Prior to the step of preparing a catalyst slurry using the obtained $AB_2O_4$ powder, the method of preparing a catalyst for oxidative dehydrogenation may further include a step of pulverizing the $AB_2O_4$ powder and classifying the pulverized $AB_2O_4$ powder so that the pulverized $AB_2O_4$ powder has a particle size of 250 μm or less, 0.1 to 250 μm, 0.1 to 75 μm, 45 μm or less, 45 to 250 μm, or 100 to 250 μm, preferably 70 μm or less, 50 μm or less, or 45 μm or less. Within this range, the catalytic activity of the $AB_2O_4$ powder is excellent, and thus the conversion rate of butene and selectivity for butadiene may be improved.

Pulverization and classification is a process of finely grinding the powder by applying a mechanical force to obtain the $AB_2O_4$ powder having a desired average particle diameter, and may be performed by a conventional method and apparatus for pulverization and classification, without being limited thereto.

After the $AB_2O_4$ powder is prepared, the $AB_2O_4$ powder is dispersed in distilled water to obtain a catalyst slurry having a concentration of 5 to 60% by weight, preferably 5 to 35% by weight, more preferably 10 to 30% by weight. When the concentration of the catalyst slurry is within this range, a coating process described later may be easily performed, and a catalyst having excellent activity may be provided.

When necessary, a binder, which includes one or more selected from aluminum-silicate, methylcellulose, and hydroxypropyl methylcellulose, is selectively included when the catalyst slurry is prepared. The binder may be added in an amount of 30 parts by weight or less or 0.1 to 20 parts by weight based on 100 parts by weight of the $AB_2O_4$.

More preferably, in the method of preparing the catalyst, the catalyst may be a binder-free catalyst. In this case, side reaction, which may be caused by a binder, does not occur during preparation of butadiene, and thus the selectivity and yield of butadiene may be improved.

The method of coating a porous support with the catalyst slurry is not particularly limited, and a conventional method of coating a porous support with a catalyst slurry, which is commonly used in the art to which the present invention pertains, may be used as the method of coating the porous support. For example, the coating may be performed using dip coating, wash coating, spray coating, impregnation, and the like.

As a specific example, after the catalyst slurry is prepared, a coating step, in which a porous support is fed into an extruder for coating, an impregnator, a rotatable chamber, or a mixer and then the catalyst slurry is fed into the apparatus while operating the apparatus, may be performed. When the porous support is coated with the catalyst slurry according to this method, catalyst waste may be minimized, and the porous support may be evenly and uniformly coated. In addition, when a reactor for oxidative dehydrogenation is filled with the catalyst, loss of an active ingredient may be minimized.

The method of feeding the catalyst slurry when the coating is performed is not particularly limited, and the catalyst slurry may be fed according to batch feed, multi-stage feed, continuous feed, injection feed, spray feed and the like. To minimize catalyst waste and make the coating uniform, multi-stage feed, continuous feed, injection feed, and spray feed are suitable.

For example, the coating may be performed at 15 to 90° C. or 50 to 80° C.

The catalyst for oxidative dehydrogenation according to the present invention may be used to prepare 1,3-butadiene from normal butene. Hereinafter, the method of performing oxidative dehydrogenation according to the present invention will be described in detail.

The method of performing oxidative dehydrogenation according to the present invention may include a step, in which oxidative dehydrogenation is performed by passing reactants including oxygen and a C4 mixture containing normal butene through a reactor filled with the catalyst for oxidative dehydrogenation.

As a specific example, the method of performing oxidative dehydrogenation according to the present invention may include i) a step of filling a reactor with a catalyst for oxidative dehydrogenation; and ii) a step, in which oxidative dehydrogenation is performed by continuously passing reactants including oxygen and a C4 mixture containing normal butene through the catalyst layer of a reactor filled with the catalyst.

For example, the method of performing oxidative dehydrogenation according to the present invention may be a method of preparing butadiene.

For example, the catalyst may be packed in a reactor in a stationary phase, and the type of the reactor is not particularly limited, and a metal tubular reactor, a multitubular reactor, a plate reactor, and the like may be used as the reactor.

For example, the catalyst may be packed in an amount of 10 to 90% by volume based on the total volume of the interior of the reactor.

For example, the C4 mixture includes one or more selected from normal butene isomers including 2-butene (trans-2-butene and cis-2-butene) and 1-butene, and may optionally further include normal butane or C4 raffinate-3.

For example, the reactants may further include one or more selected from air, nitrogen, steam, and carbon dioxide, preferably nitrogen and steam.

As a specific example, the reactants may include a C4 mixture, oxygen, steam, and nitrogen in a molar ratio of 1:0.1 to 1.5:1 to 15:0.5 to 10, 1:0.5 to 1.2:5 to 12:0.5 to 5, 1:1.0 to 1.2:5 to 12:0.5 to 5, or 1:1.2 to 1.5:5 to 12:0.5 to 5. In addition, the method of preparing butadiene according to the present invention is advantageous in that reaction efficiency is excellent and the amount of waste water generated is reduced even though steam is used in small quantities, i.e., steam is used in an amount of 1 to 10 or 5 to 10 mol based on 1 mol of the C4 mixture. Thus, the waste water treatment cost and the energy consumed in the process may be reduced.

For example, the oxidative dehydrogenation reaction may be performed at a reaction temperature of 250 to 500° C., 300 to 450° C., 320 to 400° C., or 330 to 380° C. Within this range, reaction efficiency may be improved without significantly increasing energy consumption, and thus the productivity of butadiene may be increased.

For example, the oxidative dehydrogenation reaction may be performed at a gas hourly space velocity (GHSV) of 50 to 2,000 $h^{-1}$, 50 to 1,500 $h^{-1}$, or 50 to 1,000 $h^{-1}$ based on normal butene. Within this range, reaction efficiency is excellent, and thus conversion rate, selectivity, and yield may be excellent.

Hereinafter, the present invention will be described in more detail with reference to the following preferred examples. However, these examples are provided for illustrative purposes only and should not be construed as limiting the scope and spirit of the present invention. In addition, it will be apparent to those skilled in the art that various changes and modifications may be made without departing from the spirit and scope of the present invention, and such changes and modifications are also within the scope of the appended claims.

Examples 1 to 5

1. Preparation of $ZnFe_2O_4$ Powder

A metal precursor aqueous solution containing 2 L of distilled water, 288.456 g of zinc chloride ($ZnCl_2$), and 1,132.219 g of iron chloride ($FeCl_3$) was prepared. The metal precursor solution was added dropwise to a coprecipitation bath containing 2 L of distilled water, and at the same time, 9 wt % aqueous ammonia was added thereto to adjust the pH to 8. To obtain a sample having a uniform composition, all of the metal precursor solution was added dropwise with stirring for 1 hour using an agitator, aged for 1 hour, and then the solution was filtered to separate precipitate. The separated precipitate was dried for 16 hours, and then burned at 650° C. to obtain $ZnFe_2O_4$ powder, and the obtained powder was pulverized.

Figure 1B:
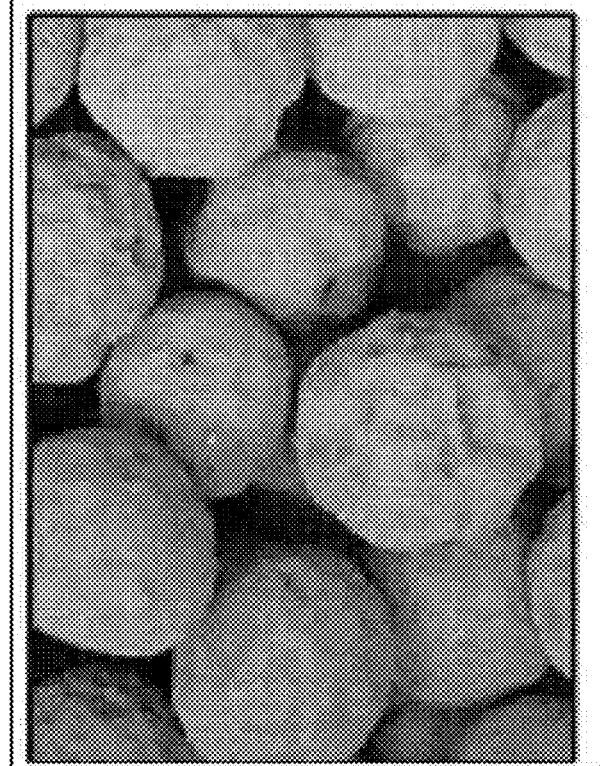

2. Preparation of Coating Catalyst $ZnFe_2O_4$ powder prepared according to the ratio shown in Table 1 was dispersed in distilled water to obtain a catalyst slurry having a concentration of about 10 to 30 wt %. Alumina balls having an average particle diameter of 5 mm and a packing density of 1.1 $g/cm^3$ were coated with the prepared catalyst slurry. The coating process was performed in a cylinder or chamber set at a temperature of 50 to 80° C. After the coating process was completed, a coating catalyst was prepared by drying the catalyst slurry-coated alumina balls in an oven at 90 to 120° C. so that distilled water was evaporated. Images showing the surface and cross-section of the prepared coating catalyst are included in FIGS. 1A and 1B. As shown in FIGS. 1A and 1B, it can be confirmed that the surface and inner pores of the coating catalyst according to the present invention are evenly coated with the active ingredient ($ZnFe_2O_4$).

3. Oxidative Dehydrogenation

Oxidative dehydrogenation of butene was performed using the coating catalyst prepared as described above, and specific reaction conditions are as follows. The ratio of reactants and gas hourly space velocity (GHSV) were determined on the basis of normal butene contained in a C4 mixture.

The C4 mixture containing trans-2-butene and cis-2-butene, oxygen, steam, and nitrogen as reactants were mixed in a molar ratio of 1:1:5:4. At this time, the amount of each of the C4 mixture, oxygen, and nitrogen was controlled using a mass flow controller, and the injection rate of steam was controlled using a liquid pump. In addition, the prepared coating catalyst was packed in a tubular reactor in a stationary phase. The feed rate of reactants was set so that a gas hourly space velocity (GHSV) was 120 $h^{-1}$ based on normal butene in the C4 mixture. The reaction temperature was set as shown in Table 1 below.

Comparative Example 1

$ZnFe_2O_4$ powder having an average particle diameter of 1 mm was prepared in the same manner as in the examples. Then, oxidative dehydrogenation was performed in the same manner as in the examples, except that 4 wt % $ZnFe_2O_4$ powder and 96 wt % alumina balls were mixed, diluted, and packed in a fixed bed reactor without a coating process.

Comparative Example 2

A coating catalyst was prepared and oxidative dehydrogenation was performed in the same manner as in the examples, except that the content of $ZnFe_2O_4$ coated on alumina balls was adjusted to 3 wt %.

Comparative Example 3

A coating catalyst was prepared in the same manner as in the examples, except that the content of $ZnFe_2O_4$ coated on alumina balls was adjusted to 30 wt %. In this case, after the coating process was completed, the $ZnFe_2O_4$ powder was separated from the alumina balls, and the coating was not maintained, such that the catalyst cannot be applied to oxidative dehydrogenation.

Reference Example 1

A coating catalyst was prepared in the same manner as in the examples, except that aluminum silicate as a binder was additionally added in an amount of 5.26 parts by weight based on 100 parts by weight of $ZnFe_2O_4$ powder when a catalyst slurry is prepared and the content of $ZnFe_2O_4$ powder coated on alumina balls was adjusted to 14 wt %.

Experimental Example

Materials generated by oxidative dehydrogenation using the catalysts according to the examples, comparative examples, and reference example were analyzed using gas chromatography. The conversion rate of butene and the yield and selectivity of 1,3-butadiene were calculated according to Equations 2, 3, and 4 below, respectively. The analysis results for the materials are shown in Table 1 below.

Conversion rate (%)=[(Number of moles of butene reacted)/(Number of moles of butene supplied)]×100     [Equation 2]

Selectivity (%)=[(Number of moles of 1,3-butadiene or $CO_X$ generated)/(Number of moles of butene reacted)]×100     [Equation 3]

Yield (%)=[(Number of moles of 1,3-butadiene generated)/(Number of moles of butene supplied)]×100     [Equation 4]

In Table 1, X represents the content of $ZnFe_2O_4$ based on 100% by weight of the total amount of $ZnFe_2O_4$ and the porous support, and * represents the case wherein alumina balls are not coated with $ZnFe_2O_4$ powder and 4 wt % of the $ZnFe_2O_4$ powder and 96 wt % of the alumina balls are diluted and packed in a reactor. As shown in Table 1, when oxidative dehydrogenation is performed using a coating catalyst having a composition satisfying Equation 1 (Examples 1 to 5), compared with Comparative Example 1, in which the porous support is not coated with the active ingredient and the active ingredient is mixed, diluted, and packed in a reactor, the conversion rate of butene, the selectivity and yield of butadiene, and the conversion rate of oxygen are excellent.

In addition, when the content of the active ingredient is within the range of 7 to 27 wt %, the coating catalyst according to the present invention maintains high catalytic activity over a wide temperature range. Therefore, the conversion rate of butene and the selectivity and yield of 1,3-butadiene are excellent.

On the other hand, when the content of the active ingredient coated on the porous support is 3 wt %, that is, the coating ratio is low, it can be confirmed that the catalytic activity is significantly lower than Example 1 having the same reaction conditions. When the content of the active ingredient is 30 wt %, that is, the coating ratio exceeds the range of the present invention, coating is not maintained, such that the catalyst cannot be applied to oxidative dehydrogenation.

In addition, in the case of Reference Example 1, in which a binder was included when a coating catalyst was prepared, selectivity for $CO_X$ as a side reaction material was high.

Additional Example 1

A coating catalyst was prepared, and oxidative dehydrogenation was performed in the same manner as in Example 3, except that a support having a packing density of 3 g/cm$^3$ was used.

Additional Example 2

A coating catalyst was prepared, and oxidative dehydrogenation was performed in the same manner as in Example 3, except that a support having a packing density of 0.4 g/cm$^3$ was used.

TABLE 1

| Reaction conditions | GHSV/mole ratio of butene:oxygen:steam:nitrogen = 120/1:1:5:4 | | | | | | | |
|---|---|---|---|---|---|---|---|---|
| | Examples | | | | | Comparative Examples | | Reference Example |
| Classification | 1 | 2 | 3 | 4 | 5 | 1 | 2 | 3 |
| X ($ZnFe_2O_4$ content, wt %) | 7 | 9 | 14 | 18 | 27 | 4* | 3 | 14 |
| Reaction temperature (° C.) | 385 | 355 | 345 | 335 | 325 | 350 | 385 | 400 |
| Butene Conversion rate (%) | 93.9 | 88.4 | 88.3 | 86.4 | 82.7 | 87.6 | 30.4 | 74 |
| 1,3-butadiene selectivity (%) | 89.7 | 88.6 | 88.5 | 88.5 | 86.6 | 88.4 | 93.2 | 84.9 |
| 1,3-butadiene yield (%) | 84.2 | 78.3 | 78.1 | 76.5 | 71.6 | 77.4 | 28.4 | 63 |
| $CO_x$ selectivity (%) | 9.5 | 10.0 | 10.1 | 10.0 | 12.0 | 9.5 | 5.0 | 13.8 |

TABLE 2

| Reaction conditions | GHSV/mole ratio of butene:oxygen:steam:nitrogen = 120/1:1:5:1 Additional Examples | |
|---|---|---|
| Classification | 1 | 2 |
| Butene conversion rate (%) | 49.0 | 80.8 |
| 1,3-butadiene selectivity (%) | 94.6 | 86.7 |
| 1,3-butadiene yield (%) | 46.3 | 70.0 |
| $CO_x$ selectivity (%) | 4.1 | 12.0 |

Additional Example 3

A coating catalyst was prepared, and oxidative dehydrogenation was performed in the same manner as in Example 3, except that a support having a packing density of 0.8 g/cm³ was used.

Additional Example 4

A coating catalyst was prepared, and oxidative dehydrogenation was performed in the same manner as in Example 3, except that a support having a packing density of 1.5 g/cm³ was used.

TABLE 3

| Reaction conditions | GHSV/mole ratio of butene:oxygen:steam:nitrogen = 120/1:1:5:1 Additional Examples | |
|---|---|---|
| Classification | 3 | 4 |
| Butene conversion rate (%) | 86.5 | 86.7 |
| 1,3-butadiene selectivity (%) | 88.6 | 87.5 |
| 1,3-butadiene yield (%) | 76.6 | 75.9 |
| $CO_x$ selectivity (%) | 10.0 | 11.2 |

As shown in Tables 2 and 3, it can be confirmed that the conversion rate of butene and the selectivity and yield of butadiene vary depending on the packing density of the support according to the present invention. More specifically, when the packing density of the support is too low or too high as in Additional Examples 1 and 2, the conversion rate of butene or the yield of butadiene is lowered. When the packing density of the support is within the range of 0.8 to 1.5 g/cm³ as in Additional Examples 3 and 4, the conversion rate of butene and the selectivity and yield of butadiene are excellent.

The invention claimed is:

1. A method of preparing a catalyst for oxidative dehydrogenation, comprising:
    preparing a metal oxide $AB_2O_4$ powder as an active ingredient for oxidative dehydrogenation, wherein:
        A is one or more metals selected from the group consisting of copper (Cu), radium (Ra), barium (Ba), strontium (Sr), calcium (Ca), beryllium (Be), zinc (Zn), magnesium (Mg), manganese (Mn), and cobalt (Co); and
        B is iron (Fe);
    pulverizing the metal oxide $AB_2O_4$ powder to produce a pulverized $AB_2O_4$ powder and classifying the pulverized $AB_2O_4$ so that the pulverized $AB_2O_4$ powder has a particle size of 0.1 to 75 µm;
    preparing a catalyst slurry by dispersing the pulverized metal oxide $AB_2O_4$ powder in distilled water;
    coating a porous support having an average pore size of 50 to 200 µm with the catalyst slurry; and
    drying the catalyst slurry-coated porous support to obtain a catalyst for oxidative dehydrogenation,
    wherein the obtained catalyst has a composition satisfying Equation 1 below:

$$X \text{ wt \%} + Y \text{ wt \%} = 100 \text{ wt \%}, \quad \text{[Equation 1]}$$

wherein X represents a content of metal oxide $AB_2O_4$ and is 5 or more and less than 30, and Y represents a content of the porous support and is more than 70 and 95 or less.

2. The method according to claim 1, wherein preparing the metal oxide $AB_2O_4$ powder comprises:
    preparing a metal precursor aqueous solution comprising a metal precursor A and a metal precursor B;
    adding the metal precursor aqueous solution and a basic aqueous solution for maintaining pH at 7 to 10 to a coprecipitation bath to coprecipitate metal A and metal B; and drying and burning the coprecipitation solution after completion of coprecipitation.

3. The method according to claim 2, wherein the basic aqueous solution is one or more selected from aqueous ammonia and an aqueous solution of sodium hydroxide.

4. The method according to claim 1, wherein the catalyst is a binder-free catalyst.

5. The method according to claim 1, wherein the porous support has an average particle diameter of 3 mm or more, and is in a form of a sphere, pellet, or hollow bar.

6. The method according to claim 1, wherein the porous support is one or more selected from the group consisting of alumina, silica, and zirconia.

7. The method according to claim 1, wherein the porous support has a packing density of 0.4 to 3 g/cm³.

* * * * *

UNITED STATES PATENT AND TRADEMARK OFFICE
CERTIFICATE OF CORRECTION

PATENT NO. : 10,888,844 B2
APPLICATION NO. : 16/301403
DATED : January 12, 2021
INVENTOR(S) : Myung Ji Suh et al.

Page 1 of 1

It is certified that error appears in the above-identified patent and that said Letters Patent is hereby corrected as shown below:

In the Claims

At Column 12, Line 22 please correct Claim 1 as follows:
1. A method of preparing a catalyst for oxidative dehydrogenation, comprising:
  preparing a metal oxide $AB_2O_4$ powder as an active ingredient for oxidative dehydrogenation, wherein:
    A is one or more metals selected from the group consisting of copper (Cu), radium (Ra), barium (Ba), strontium (Sr), calcium (Ca), beryllium (Be), zinc (Zn), magnesium (Mg), manganese (Mn), and cobalt (Co); and
    B is iron (Fe);
  pulverizing the metal oxide $AB_2O_4$ powder to produce a pulverized $AB_2O_4$ powder and classifying the pulverized $AB_2O_4$ powder so that the pulverized $AB_2O_4$ powder has a particle size of 0.1 to 75 μm;
  preparing a catalyst slurry by dispersing the pulverized metal oxide $AB_2O_4$ powder in distilled water;
  coating a porous support having an average pore size of 50 to 200 μm with the catalyst slurry; and
  drying the catalyst slurry-coated porous support to obtain a catalyst for oxidative dehydrogenation,
  wherein the obtained catalyst has a composition satisfying Equation 1 below:
    X wt% + Y wt% = 100 wt%,      [Equation 1]
  wherein X represents a content of metal oxide $AB_2O_4$ and is 5 or more and less than 30, and Y represents a content of the porous support and is more than 70 and 95 or less.

Signed and Sealed this
Ninth Day of February, 2021

Drew Hirshfeld
*Performing the Functions and Duties of the
Under Secretary of Commerce for Intellectual Property and
Director of the United States Patent and Trademark Office*